(12) United States Patent
Kalhous et al.

(10) Patent No.: US 9,440,658 B2
(45) Date of Patent: Sep. 13, 2016

(54) SYSTEM AND METHOD FOR CONTROLLING AN AUTOMOBILE USING EYE GAZE DATA

(71) Applicant: GM GLOBAL TECHNOLOGY OPERATIONS LLC, Detroit, MI (US)

(72) Inventors: Amanda J. Kalhous, Ajax (CA); Norman J. Weigert, Whitby (CA); Mark A. Manickaraj, Scarborough (CA)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 93 days.

(21) Appl. No.: 14/269,902

(22) Filed: May 5, 2014

(65) Prior Publication Data

US 2015/0314792 A1 Nov. 5, 2015

(51) Int. Cl.
| | | |
|---|---|---|
| B60W 50/00 | (2006.01) | |
| A61B 5/11 | (2006.01) | |
| B60R 25/25 | (2013.01) | |
| G06K 9/00 | (2006.01) | |
| H04N 7/18 | (2006.01) | |
| A61B 5/117 | (2016.01) | |
| B60R 16/037 | (2006.01) | |

(52) U.S. Cl.
CPC ............... *B60W 50/00* (2013.01); *A61B 5/117* (2013.01); *B60R 16/037* (2013.01); *B60R 25/25* (2013.01); *G06K 9/00617* (2013.01); *H04N 7/18* (2013.01)

(58) Field of Classification Search
CPC .................................................... B60R 16/037
See application file for complete search history.

(56) References Cited

U.S. PATENT DOCUMENTS

| | | | | |
|---|---|---|---|---|
| 7,864,029 B2* | 1/2011 | Huang | ............... | B60R 25/04 340/426.1 |
| 8,761,998 B2* | 6/2014 | Chen | ............... | B60R 16/037 701/36 |
| 8,937,528 B2* | 1/2015 | Protopapas | ............... | B60R 25/25 340/5.52 |
| 2007/0219675 A1* | 9/2007 | Uchida | ............... | B60R 16/037 701/1 |
| 2010/0036560 A1* | 2/2010 | Wright | ............... | B60R 16/037 701/36 |
| 2013/0141578 A1* | 6/2013 | Chundrlik, Jr. | ............... | H04N 7/181 348/148 |
| 2014/0310788 A1* | 10/2014 | Ricci | ............... | G07C 9/00158 726/6 |
| 2015/0120135 A1* | 4/2015 | Lawrenson | ............... | B60W 50/085 701/36 |
| 2015/0131160 A1* | 5/2015 | Kwak | ............... | G02B 27/0149 359/631 |

* cited by examiner

*Primary Examiner* — Todd Melton
(74) *Attorney, Agent, or Firm* — Lorenz & Kopf, LLP

(57) ABSTRACT

A system or method capable of using automobile camera system data to generate biometric information for the use in identifying authorized drivers and customizing and controlling automobile components. The system is versatile enough to distinguish between a new or unauthorized person in the automobile and respond accordingly.

12 Claims, 4 Drawing Sheets

SYSTEM AND METHOD FOR CONTROLLING AN AUTOMOBILE USING EYE GAZE DATA

TECHNICAL FIELD

Embodiments of the subject matter described herein relate generally to automobile control systems, and more particularly, to the use of eye gaze data for customization and control of automobile components.

BACKGROUND

One aspect of the rapid evolution of automobile system design is the number of adjustable components and settings available to personalize or customize the automobile environment. Often, more than one driver uses an automobile, requiring the components to be re-adjusted each time the driver changes. In addition, some drivers may have multiple customization preferences, such as daytime driving and nighttime driving. Generally, the adjustment of component settings is by electronic control, which has fostered the ability to store driver component setting preferences in a driver record in a database.

Traditional automobile systems rely on receiving a prompt or query from a driver to initiate component customization. The prompt or query is currently provided either manually, such as when the driver selects an automobile button, or it is provided electronically, such as a signal transmission via a key fob, remote cell phone, or other similar device. As such, traditional automobile systems rely on a device that is external to the vehicle and are vulnerable to security breaches such as a person without authorization obtaining the automobile key-code, the controlling key fob, or the controlling remote cell phone and then operating the automobile. Camera systems have been introduced into automobile cabins for various purposes such as drowsiness detection and the eye gaze data collected by the camera system can further be utilized to provide uniquely identifying biometric information.

Consequently, a system or method capable of using automobile camera system data to generate biometric information for the use in identifying authorized drivers and customizing and controlling automobile components is desirable. The system is versatile enough to distinguish between a new or unauthorized person in the automobile and respond accordingly.

BRIEF SUMMARY

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

A method is provided for automobile customization and control. The iris image data of a driver is obtained and converted into biometric information. The biometric information is used to search a database for matching biometric information. When matching biometric information is located in the database, a driver record including at least one driver preference setting for an automobile component is retrieved. An automobile component is adjusted according to the driver preference.

A system is provided for automobile customization and control. The system includes an automobile camera system configured to locate a driver's eyes and generate iris image data, a database including at least one driver record and an automobile component. The system also includes a processor coupled to the camera system, automobile component, and the database, and configured to (1) convert iris image data to biometric information, (2) search the database for matching biometric information, (3) retrieve from the database, when the database has matching biometric information, an associated driver record including a driver preference setting for the automobile component, and (4) adjust the automobile component according to the driver preference.

Another method is provided for automobile customization and control. Iris image data of a driver is obtained and converted into biometric information. A database is searched, looking for a match of the biometric information. When there is no matching biometric information, a first driver record including a driver preference for a component setting is generated, and a component is adjusted according to the driver preference in the first record.

Other desirable features will become apparent from the following detailed description and the appended claims, taken in conjunction with the accompanying drawings and this background.

BRIEF DESCRIPTION OF THE DRAWINGS

A more complete understanding of the subject matter may be derived by referring to the following Detailed Description and Claims when considered in conjunction with the following figures, wherein like reference numerals refer to similar elements throughout the figures, and wherein:

DETAILED DESCRIPTION

Figure 1:
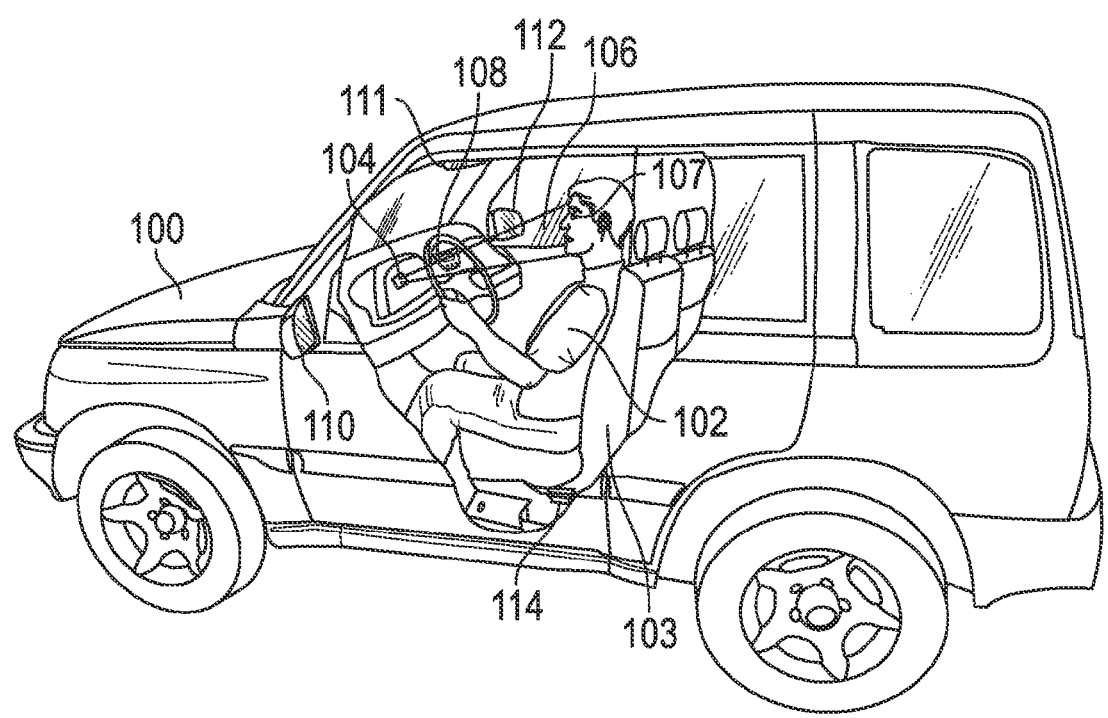
FIG. 1 is a cut-away illustration of a side of an automobile, with a driver seated in the driver's seat.

The following Detailed Description is merely exemplary in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over any other implementations. Furthermore, there is no intention to be bound by any expressed or implied theory presented in the preceding Technical Field, Background, Brief Summary or the following Detailed Description.

For the sake of brevity, conventional techniques related to graphics and image processing, sensors, and other functional aspects of certain systems and subsystems (and the individual operating components thereof) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

Techniques and technologies may be described herein in terms of functional and/or logical block components and with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. The memory locations where data bits are maintained are physical locations that have particular electrical, magnetic, optical, or organic properties corresponding to the data bits. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

The following descriptions may refer to elements or nodes or features being "coupled" together. As used herein, unless expressly stated otherwise, "coupled" means that one element/node/feature is directly or indirectly joined to (or directly or indirectly communicates with) another element/node/feature, and not necessarily mechanically. Thus, although the drawings may depict one exemplary arrangement of elements, additional intervening elements, devices, features, or components may be present in an embodiment of the depicted subject matter. In addition, certain terminology may also be used in the following description for the purpose of reference only, and thus are not intended to be limiting.

FIG. 1 is a cut-away illustration of a side of an automobile 100 with a driver 102 seated in the driver's seat 103. Camera system 104 is shown with a detection path 106 directed to the driver's eyes 107. Also shown are several representative automobile components and/or instruments that may have adjustable settings, such as: display unit 108, side mirror 110, side mirror 112, rear-view mirror 111, and a seat control 114. The objects shown in FIG. 1 and their functions are described below.

It is readily appreciated that a modern automobile 100 may have numerous additional components and/or instruments, each with adjustable settings. For example, components may also include steering wheel position, seat positions, mirror angles, stereo channels and volumes, temperature control, satellite services, phone services, and the like. In addition, the various components may be adjusted in different ways, for example, some may adjust in a digital signal such as, "on/off," and other components may adjust in an analog scale, such as one through ten, as may be utilized for volume or temperature.

In the exemplary embodiment, camera system 104 is positioned below eye-level of driver 102, in an area behind the steering wheel, and is directed at the driver's eyes as illustrated by detection path 106; however, camera system 104 may be positioned anywhere within the automobile provided that detection path 106 is able to locate the driver's eyes. In the embodiment, the detection path has a range that extends in a substantially conical volume having a maximum diameter of about one and a half meters to about two meters. It is to be understood that although detection path 106 is depicted as a singular path defined by sharp lines extending from the camera system 104 to the driver's eyes 107, in practice it may include multiple detection paths, taper off at the edges, and/or have volumetric shapes that are not conical.

Camera system 104 is integrated into the cabin of a traditional automobile and may provide data for multiple automobile system functions. In the exemplary embodiment, camera system 104 has appropriate resolution to detect, at a minimum, the driver's irises, and provide associated data to the biometric adjust module (object 202, in connection with FIG. 2). Iris image data from camera system 104 is converted by the biometric adjust module 202 into a plurality of data points associated with uniquely identifying an individual according to his or her iris. The conversion of the iris image data into uniquely identifying information is performed in the biometric adjust module 202 according to an iris detection algorithm. A proposed iris detection algorithm is described in, John Daughman, *Daughman's Algorithm Method for Iris Recognition-A Biometric Approach*, Journal of Emerging Technology and Advanced Engineering ISSN 2250-2459 Volume 2. Issue 6, 177. June 2012.

Figure 2:
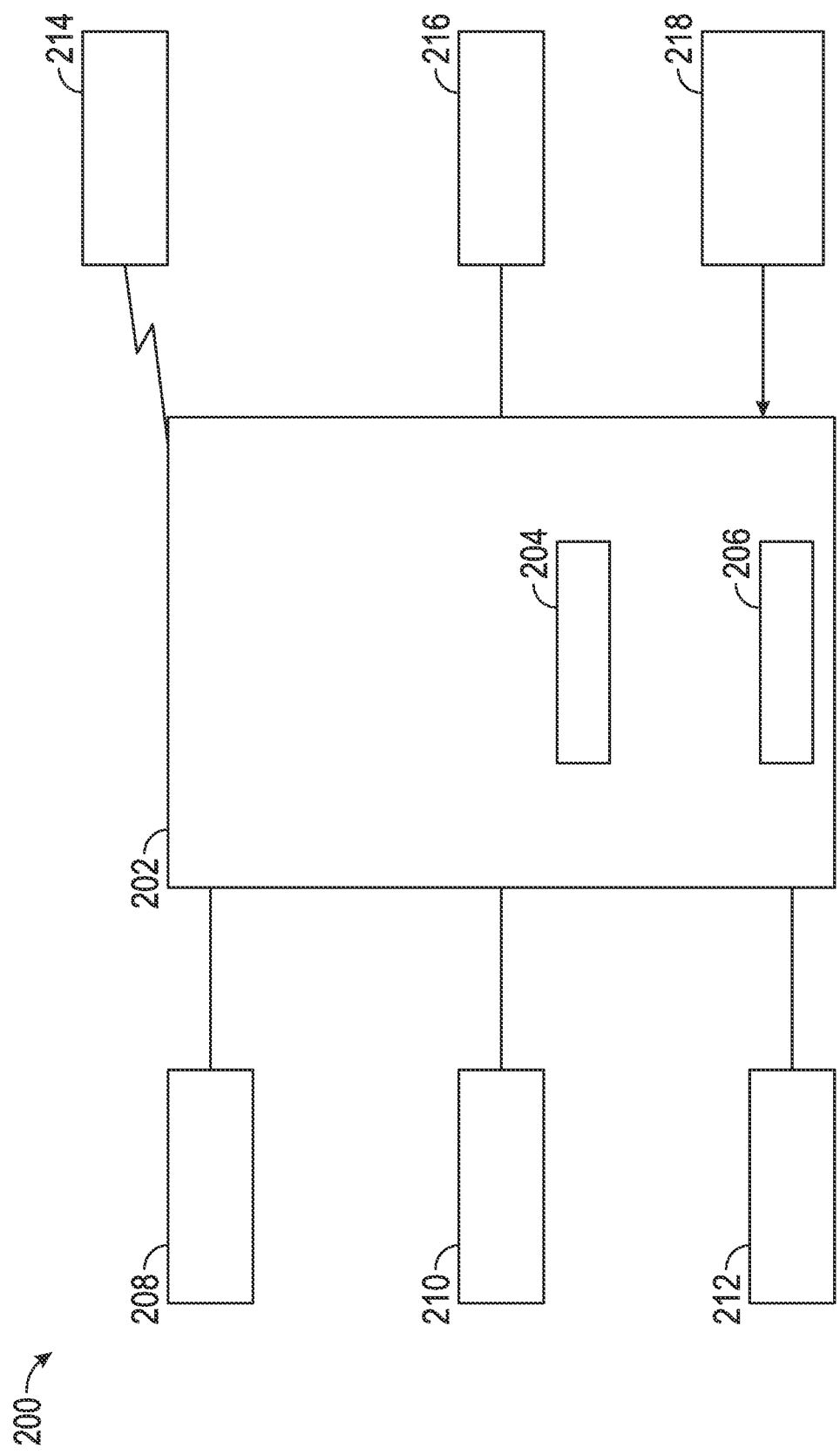
FIG. 2 is a block diagram of an automobile control system showing a biometric adjust module.

FIG. 2 is a block diagram of an automobile control system 200 showing a biometric adjust module 202 coupled to display unit 208, driver interface 210, and camera system 212. One or more wireless data sources 214 are coupled to biometric adjust module 202 and may communicate via one or more wireless protocols with biometric adjust module 202. Components 216, such as mirrors, seats, the steering wheel, etc., are coupled to biometric adjust module 202, as well as secondary authorization sources 218, the purpose and use of which are described in connection with FIG. 3. Biometric adjust module 202 includes a processor 204 and memory 206. It may be readily appreciated that, in practice, an automobile control system 200 generally has a number of additional functional blocks not shown in FIG. 2. The functions and interactions of the remaining sub-blocks are as follows.

The processor 204 may be implemented or realized with at least one general purpose processor, a content addressable memory, a digital signal processor, an application specific integrated circuit, a field programmable gate array, any suitable programmable logic device, discrete gate or transistor logic, discrete hardware components, or any combination designed to perform the functions described herein. A processor device may be realized as a microprocessor, a controller, a microcontroller, or a state machine. Moreover, a processor device may be implemented as a combination of computing devices, e.g., a combination of a digital signal processor and a microprocessor, a plurality of microprocessors, one or more microprocessors in conjunction with a digital signal processor core, or any other such configuration.

In practice, the processor 204 may be realized as an onboard component of an automobile control system or automobile management system, or it may be realized in a portable computing device that is carried into the automobile. For example, the processor 204 could be realized as the central processing unit (CPU) of a laptop computer, a tablet computer, or a handheld device.

The processor 204 may include or cooperate with an appropriate amount of memory 206 which can be realized as RAM memory, flash memory, EPROM memory, EEPROM memory, registers, a hard disk, a removable disk, a CD- ROM, or any other form of storage medium known in the art. In this regard, the memory 206 can be coupled to the processor 204 such that the processor 204 can read information from, and write information to, the memory 206. In the alternative, the memory 206 may be integral to the processor 204. In practice, a functional or logical module/component of the system described here might be realized using program code that is maintained in the memory 206. Moreover, the memory 206 can be used to store data utilized to support the operation of the system, as will become apparent from the following description.

No matter how the processor 204 is specifically implemented, it is in operable communication with the camera system 212, driver interface 210, display unit 208, at least one automobile component 216, and one or more secondary authorization sources 218. The processor 204 is configured to determine, in response to iris image data from the camera system 212, whether the driver has an existing driver record in a predetermined driver database that is stored in memory 206, and contains data entries referred to as driver records. Biometric adjust module 202 may also determine whether to generate a new driver record based on information from secondary authorization sources 218, as described in FIG. 3.

Driver records are an entry that associates a driver's identification, biometric data, and driver preferences. The driver preferences are the settings on the various automobile components and instruments. The processor 204 is configured to download the relevant driver record and to generate the system commands required to effect the adjustment of automobile components and instruments according to the preferences stored in the driver record. The processor 204 may also be configured to add a new driver's information to the driver database by creating a new driver record that associates driver identification, driver biometric information and driver preferences for component settings. The wireless data source 214 communicates with the biometric adjust module 202 via a wireless communication protocol, and in response to input from wireless data source 214 the processor 204 may edit, store or share driver records in the driver database. Example wireless communication protocols may include a 3G™ or LTE™ connection from, for example, an OnStar™ Module that resides within the automobile or is external to the automobile. In addition there may be some serial data communication between the biometric adjust module 202 and other automobile system modules.

The display unit 108, in response to commands supplied from the processor 204, selectively renders various textual, graphic, and/or iconic data, and thereby supplies visual feedback and/or prompts to the driver. It will be appreciated that the display unit 108 may be implemented using any one of numerous known display devices suitable for rendering textual, graphic, and/or iconic information in a format viewable by the driver. Non-limiting examples of such display devices include various multifunction displays (MFD), Near to Eye (NTE), projection displays, cathode ray tube (CRT) displays, and flat screen displays such as LCD (liquid crystal display) and TFT (thin film transistor) displays. The display unit 108 may additionally be implemented as a screen mounted display, or any one of numerous known technologies.

Driver interface 210 may be directly or indirectly coupled to the display unit 208; for example, in the form of a touch screen or control knobs. The driver may manually interface with the automobile control system via a touchpad or a keypad, but the driver interface 210 may also include any combination of one or more of the following: knob, microphone, wireless device such as a mobile cell phone, speech or gesture recognition modules, keyboard, touchscreen, joystick, or another suitable device adapted to receive input from a driver.

Figure 3:
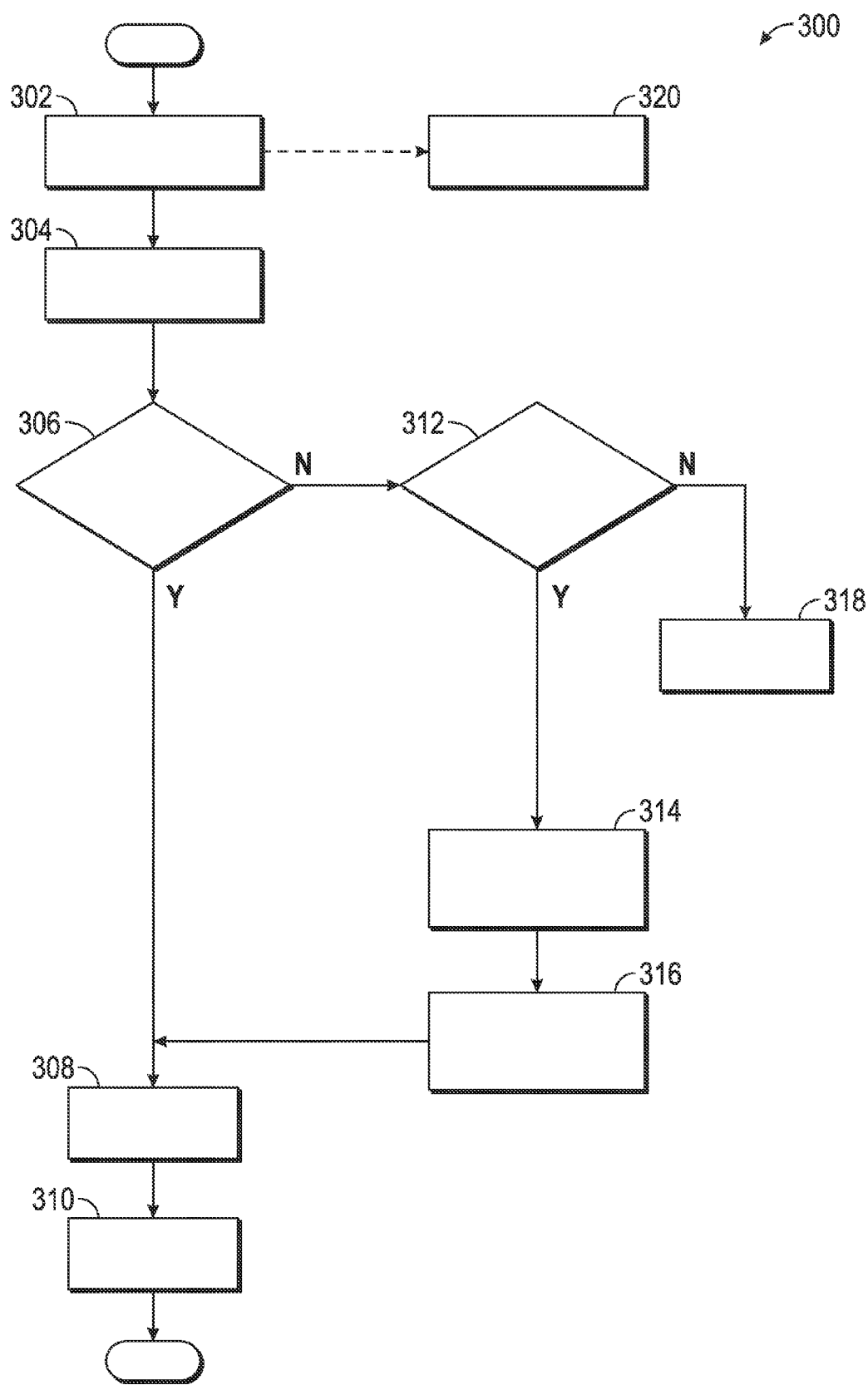
FIG. 3 is a flow chart illustrating an exemplary embodiment of a biometric adjust process for identifying a driver and customizing component settings.

FIG. 3 is a flow chart illustrating an exemplary embodiment of a biometric adjust process 300 for identifying a driver and customizing component settings. The exemplary steps provided herein may or may not be present in every embodiment, and some embodiments may have additional steps, or have the steps arranged differently. It is to be understood that processor 204 continuously monitors input from the camera system 212, driver interface 210, components 216 and wireless data source 214, and may continuously run process 300.

Process 300 begins when the camera system 212 locates the driver's eyes (STEP 302) and then collects, as images, the associated iris data. In the biometric adjust module 202, the iris image data is processed through the iris detection algorithm (STEP 304), whereby the biometric adjust module 202 generates a plurality of data points that have been determined to be unique to an individual. As used herein, the resulting iris identifying data is referred to as the "biometric information," which is the first authorization source. After the driver's eyes are located at STEP 302, the distance of the eyes above the hood-line of the automobile may optionally be used to adjust a head-up display (HUD) to a comfortable viewing height for the driver (STEP 320).

At STEP 306 processor 204 accesses the driver database stored in memory 206, utilizing the biometric information, to determine whether the driver has a driver record in the driver database. If the biometric information matches biometric information in the driver database at STEP 306, an associated driver record including identification of the driver and preferred component settings is downloaded (STEP 308), and the components are adjusted according to driver preference at STEP 310.

It is to be noted that the driver database may have multiple driver records for one driver; for example, a driver may have different customization requirements for daytime driving and nighttime driving, or for driving with children in the automobile and driving alone. Selection of the appropriate driver record may then rely on further driver interaction with process 300, and/or may rely on other automobile system information such as a GPS location, light or temperature sensor information, time of day, and the like.

If the driver database does not have an associated driver record at STEP 306, secondary authorization sources 218 may be relied upon to determine whether the driver is authorized to operate the automobile (STEP 312). Non-limiting examples of secondary authorization sources 218 include: the driver having the key fob, the driver having a device such as a mobile cell phone that is in wireless communication with the automobile, or the driver having a personal identification number or password.

If it is determined via secondary authorization sources 218 that the driver is authorized to operate the automobile, process 300 obtains driver identification and preferred component settings at STEP 314. Process 300 obtains driver preferences for component settings in multiple ways; for example, the driver may first manually adjust control settings, followed by a manual or audible confirmation or prompt that customization is complete, the driver may use voice recognition to perform the entire customization process, or the driver may rely on any combination of driver interface devices described hereinabove.

After driver preferences are obtained at STEP 314, a driver record is generated that associates the driver's identification, the driver's biometric information, and the driver's preferences; the driver record is then stored (STEP 316). The driver record is downloaded (STEP 308), and the components are adjusted according to driver preference at STEP 310.

If the driver does not already have a driver record in the driver database at STEP 306, and the driver cannot provide secondary authorization at STEP 312, process 300 may provide various security options at STEP 318. Example security options include, but are not limited to, preventing the driver from starting the ignition, sounding an alarm, and calling the police or a security service.

Figure 4:
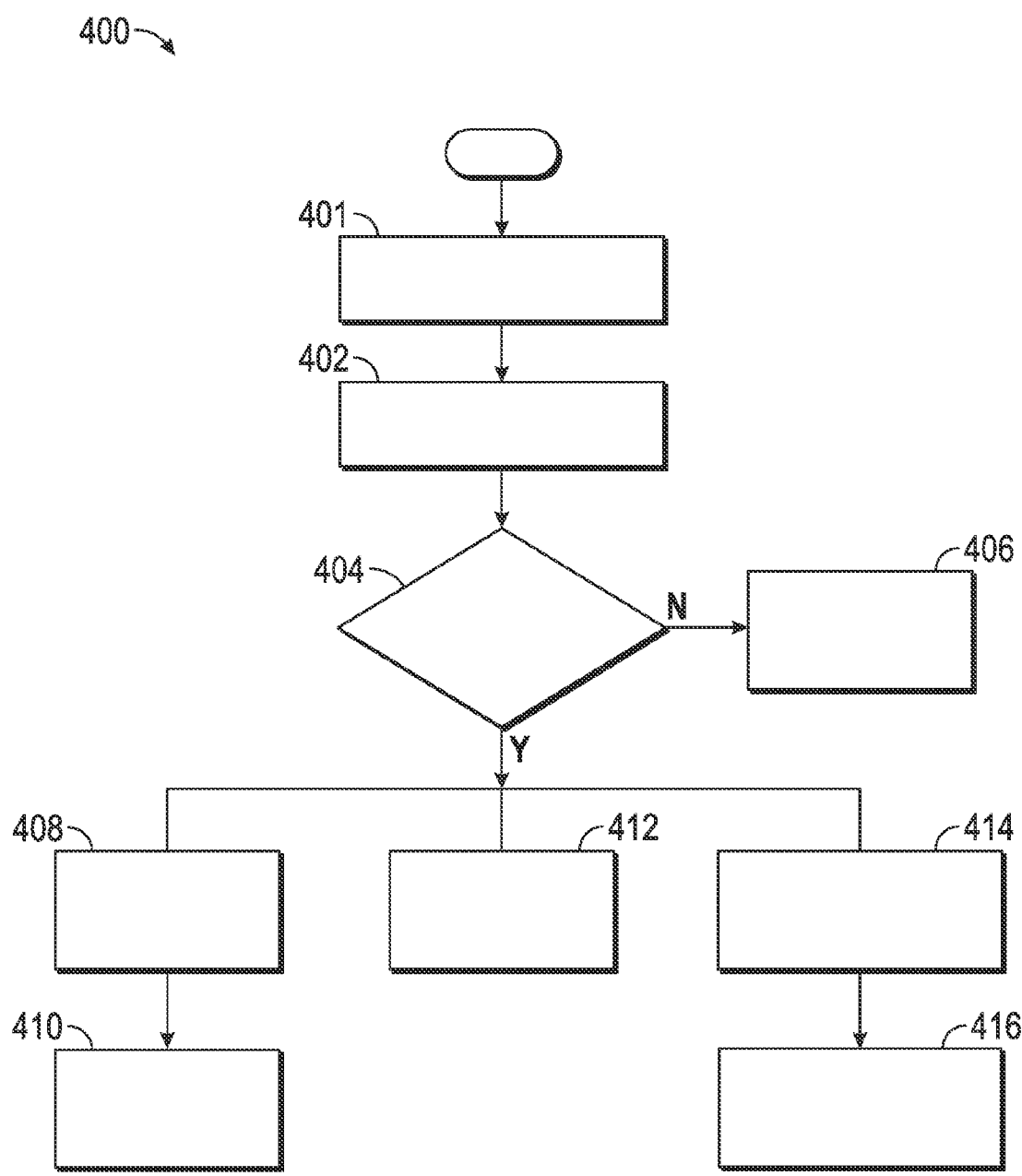
FIG. 4 is a flow chart illustrating another exemplary embodiment of a biometric adjust process for identifying a driver and customizing the driver experience.

FIG. 4 is a flow chart illustrating another exemplary embodiment of a biometric adjust process 400 for identifying a driver and customizing the driver experience. After the driver's eyes are located at STEP 401, and the iris detection algorithm generates biometric information at STEP 402, processor 204 determines whether the driver is an authorized driver (STEP 404). As described in detail hereinabove, biometric information and secondary authorization sources 218 may be utilized to determine whether the driver is authorized to operate the automobile. At STEP 406, security options such as preventing the ignition to start and triggering security alerts may occur. Security alerts may include any combination of aural sounds, calling the police or a security system, preventing the opening of doors or the trunk, etc.

If the driver is an authorized driver, various customized options may be provided, most significantly, the ability to turn on the ignition at STEP 412. In reliance upon the iris detection and identification provided by process 400, the exemplary embodiment may allow the driver to download an application at STEP 408, and may further allow the driver to authorize a purchase at STEP 410. The driver downloads and purchases applications and data by utilizing the various wireless data sources 214 using various wireless communication protocols, such as Wi-Fi, 3G™, LTE™, and Bluetooth™. Additionally, process 400 may enhance the driver's comfort and safety by, for example, detecting if too much light is in the driver's eye (STEP 414) and suggesting the use of a visor or sunglasses (STEP 416). Suggestions may be presented to the driver visually or aurally and may use any display, speaker, or driver interface device in operable communication with the automobile.

Thus, there has been provided an automobile system or method capable of using automobile camera system data to generate biometric information for the use in identifying authorized drivers and customizing and controlling automobile components. The system is versatile enough to distinguish between a new or unauthorized person in the automobile and respond accordingly.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method for automobile customization and control, the method comprising:
   obtaining iris image data of a driver;
   converting the iris image data into biometric information, wherein the biometric information is the first authorization source;
   when it is determined, using the biometric information, that the driver has a driver record in a database, (i) retrieving from the database the driver record including at least one driver preference setting for an automobile component, and (ii) adjusting the automobile component according to the driver preference; and
   when it is determined, using the biometric information, that the driver does not have a driver record in the database, determining, using secondary authorization sources whether the driver is authorized to operate the automobile; and
   when it is determined, (i) using the biometric information, that the driver does not have a driver record in the database, and (ii) using secondary authorization sources, that the driver is authorized to operate the vehicle,
      (a) obtaining a driver identification and at least one driver preference setting, and
      (b) generating a driver record including the driver identification, the biometric information, and the driver preference setting.

2. The method of claim 1, wherein secondary authorization sources include at least one of a key fob, a wireless device, a smart phone, a mobile cell phone, a password and a personal identification number.

3. The method of claim 1, further comprising storing the driver record in the driver database.

4. The method of claim 1, wherein the step of obtaining comprises generating visual or aural prompts.

5. The method of claim 1, further comprising:
   detecting the amount of light directed at the driver's eyes; and
   suggesting the use of the visor or sunglasses according to the detected amount of light.

6. The method of claim 1, further comprising authorizing, using the driver identification associated with the biometric information, the download and purchase of applications.

7. The method of claim 1, further comprising:
   determining the location of the driver's eyes above a hood-line of the automobile; and
   adjusting an automobile head-up display in accordance with the location.

8. The method of claim 1, wherein the step of retrieving an associated driver record comprises selecting from among a plurality of associated driver records in reliance on one or more of a GPS location, a light sensor, temperature sensor, and the time of day.

9. The method of claim 1, further comprising: when it is determined,
   (i) using the biometric information, that the driver does not have a driver record in the database, and
   (ii) using secondary authorization sources, that the driver is not authorized to operate the vehicle,
   preventing the automobile from starting.

10. A system for automobile customization and control, the system comprising:
    an automobile camera system configured to locate a driver's eyes and generate iris image data;
    a database including at least one driver record;
    an automobile component; and a processor coupled to the camera system, automobile component, and the database, and configured to
(1) convert iris image data to biometric information,
(2) determine, using the biometric information, whether the driver has a driver record in a database,
(3) when it is determined that the driver has a driver record in the database, (i) retrieve from the database the driver record including at least one driver preference setting for an automobile component, and (ii) adjust the automobile component according to the driver preference, and
(4) when it is determined using biometric information, that the driver does not have a driver record in the database, determine, using secondary sources, whether the driver is authorized to operate the automobile; and
when it is determined, (i) using the biometric information, that the driver does not have a driver record in the database, and (ii) using secondary authorization sources, that the driver is authorized to operate the vehicle via secondary authorization sources,
   (a) obtain a driver identification and at least one driver preference setting, and
   (b) generate a driver record including the driver identification, biometric information, and the driver preference setting.

11. The system of claim 10, wherein the processor is further configured to, when it is determined (i) using the biometric information, that the driver does not have a driver record in the database, and (ii) using secondary authorization sources, that the driver is not authorized to operate the vehicle, prevent the automobile from starting.

12. The system of claim 10, wherein the processor is further configured to adjust an automobile head-up display in accordance with a location of the driver's eyes.

* * * * *